United States Patent [19]

Lam et al.

[11] Patent Number: 5,023,179
[45] Date of Patent: Jun. 11, 1991

[54] PROMOTER ENHANCER ELEMENT FOR GENE EXPRESSION IN PLANT ROOTS

[76] Inventors: Eric Lam, Faculty House, 500 E. 63rd St., New York, N.Y. 10021; Philip N. Benfey, 325 E. 84th St., New York, N.Y. 10028; Philip M. Gilmartin, 500 E. 63rd St., New York, N.Y. 10021; Nam-Hai Chua, 32 Walworth Ave., Scarsdale, N.Y. 10583

[21] Appl. No.: 272,169

[22] Filed: Nov. 14, 1988

[51] Int. Cl.$^5$ .................... C12N 15/00; C12N 1/00; C07H 21/04; C12P 21/00
[52] U.S. Cl. .................... 435/172.3; 536/27; 435/69.1; 435/91; 435/317.1; 435/240.4; 935/35; 935/67; 800/200; 800/DIG. 43
[58] Field of Search ................ 536/27; 435/91, 172.3, 435/317.1, 69.1; 935/35

[56] References Cited

PUBLICATIONS

Poulsen et al., 1988, Mol. Gen. Genetics 214:16–23 (Sep.).
Odell et al., 1985, Nature 313:810–812.
Sanders et al., 1987, Nucleic Acids Research 15:1543–1558.
Green et al., 1987, EMBO J. 6(9):2543–2549.

*Primary Examiner*—Charles F. Warren
*Assistant Examiner*—P. Rhodes
*Attorney, Agent, or Firm*—Thomas P. McBride; Dennis R. Hoerner, Jr.; Howard C. Stanley

[57] ABSTRACT

Detection of a cellular factor from pea and tobacco which binds to a repeated pentameric motif of TGACG present in the −90 to −60 region of the CaMV 35S promoter is disclosed. Also disclosed is a 21 bp promoter element which is capable of imparting root expression capability to a rbcS-3A promoter, normally a green tissue specific promoter.

5 Claims, 4 Drawing Sheets

```
                -85                              -58
                 ┌────────────────────────────────┐
     GTGATATCTCCACTGACGTAAGGGATGACGCACAATCCCACTATC
-95                                                     -51
     CACTATAGAGGTGACTGCATTCCCTACTGCGTGTTAGGGTGATAG
         └────────────────────────────────┘
        -90                              -59
```

FIGURE 1

WT      5'ATCTCCACTGACGTAAGGGATGACGCACAATCCCACTATC
        -85                                              -58 as-1b

TG                              GG

5'ATCTCCACTGACGTAAGGGATGACGCACAATCCCACTATC
        -86                                              -55 as-1c

GT                      CT

5'ATCTCCACTGACGTAAGGGATGACGCACAATCCCACTATC

FIGURE 2

WT      CT<u>GAC</u>GTAAGGGAT<u>GAC</u>GCAC as-1c   CTG<u>GT</u>GTAAGGGAT<u>CT</u>CGCAC

FIGURE 4

PROMOTER ENHANCER ELEMENT FOR GENE EXPRESSION IN PLANT ROOTS

The present invention relates to genetic engineering and more specifically to tissue specific enhancement of gene expression in plants.

BACKGROUND OF THE INVENTION

Cauliflower mosaic virus (CaMV) is a double-stranded DNA plant virus. It contains two promoters responsible for the production of transcripts of 35S and 19S in size in infected plants (1). The 35S promoter has been studied in considerable detail (2, 3). This promoter is not only active in isolated protoplasts of monocots and dicots (4) but is also expressed in all organs of transgenic petunia and tobacco in the absence of any viral protein (2, 5). The high activity of the 35S promoter and its apparent constitutive expression have made it an attractive model system to investigate cis regulatory elements for plant gene transcription.

Several 5' deletion mutants of the 35S promoter have been analyzed in transformed tobacco calli as well as in transgenic tobacco plants (2, 6). Whereas a promoter containing only 46 bp of 5' sequence was sufficient for accurate transcription initiation, sequences between −46 and −105 can significantly increase the expression level. In a recent detailed analysis of the 35S promoter (−343 to +9) in vivo, it was reported that an internal deletion of the −107 to −46 region leads to a 60% decrease in transcription activity (6). More dramatically, the activity of an upstream element (−343 to −208) is only detectable when fused to the 35S promoter deleted to −90 but not to the −46. Since the -90 promoter element has little activity in vivo except in root (7), these data suggest the existence of an element in the −90 to −46 region of the 35S promoter, that modulates the activity of elements upstream. Results from transient assays of deletion derivatives of the 35S promoter have also indicated the presence of an element 3' of −90 that is required for expression of upstream elements (3). Because of the proximity of this region to the TATA box, it has been suggested that the relevant sequences are among the three CAAT box-like motifs located between −90 and −46 (2, 3).

BRIEF DESCRIPTION OF THE DRAWINGS

FIG. 1 shows the nucleotide sequence for the ASF-1 binding site from the CaMV35S promoter.

FIG. 2 shows the nucleotide sequences for mutant ASF-1 binding site mutants as /band as/c.

FIG. 4 shows the sequence of the 21 bp promotor element of the present invention.

STATEMENT OF THE INVENTION

Figure 3:
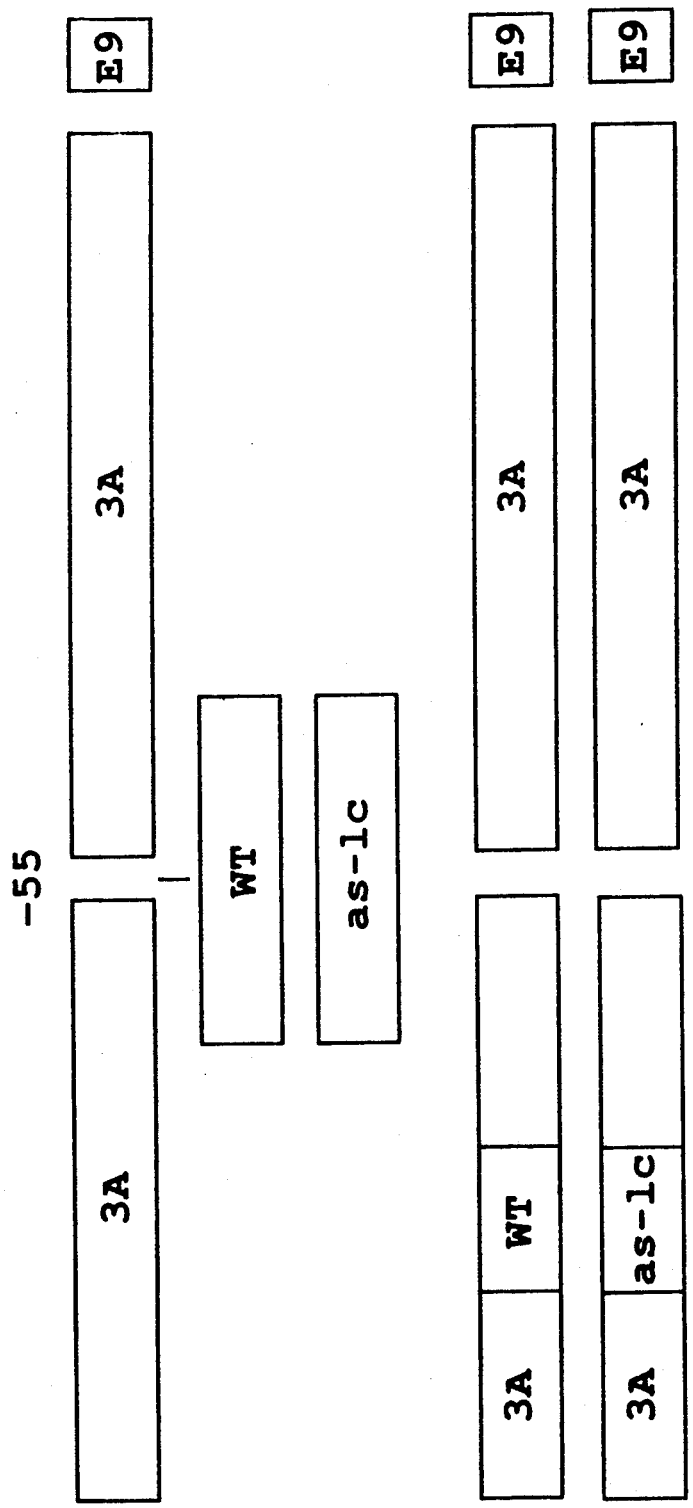
FIG. 3 shows the constructs (I-IV) used to demonstrate root enhancement expression of the rbcS-3A promoter.

In one aspect, the present invention involves the discovery of a factor from whole cell extracts of etiolated peas. The factor has been named activation sequence factor 1 (ASF-1). In yet another aspect, the present invention involves the discovery of a binding site for the ASF-1 factor. The binding site covers two of the three putative CAAT-box sequences as well as two pentanucleotide repeats, TGACG, separated by seven base pairs. It has been further demonstrated that the organ specificity of a promoter such as the green tissue specific promoter, the rbcS-3A promoter, can be altered by insertion of a single binding site for factor ASF−1.

The CaMV 35S promoter from −343 to +8 was used to assay for sequence specific DNA binding activities in plant extracts since this fragment of the CaMV genome is known to function as a strong plant promoter in vivo. One single binding site of a factor, now known as ASF-1, was first detected by DNase I-footprinting with a whole cell extract from etiolated peas. The probe used for this assay was prepared from a pEMBL 12x clone containing this fragment with HindIII and XhoI sites at the respective borders. Three micrograms of this plasmid were cut with XhoI and then labeled at this site by Klenow fill in with all four [alpha $^{32}$P]-dNTPs. Subsequently, the probe is cut with either HindIII or XmnI to generate either a 350 bp or 138 bp fragment, respectively. To map the binding site on the other strand a subclone of the −130 to −46 region of the 35S promoter in pEMBL 12x was used in an identical fashion. Referring to FIG. 1, the protected region extends from −86 to −59 on the sense strand and from −91 to −60 on the antisense strand. The binding site has been further localized to a 21 bp sequence of the sense strand having the sequence:

5'-CTGACGTAAGGGATGACGCAC-3'

To determine what sequences are essential for binding of ASF-1 two consecutive bases within each of the putative CAAT-box motifs (mutant as-1b) or within each of the TGCG repeats (mutant as-1c) were altered (see FIG. 2). The binding affinities of the two mutants were compared with that of the wild type sequence. It was determined that as-1b binds the factor with reproducibly higher affinity than the wild type sequence. Mutant as-1he other hand, is not protected by ASF-1 even at high extract concentrations. Competition experiments using the DNase I footprint assay revealed that both the wild-type sequence and as-1b compete very well for binding to the wild-type element at 50 fold molar excess whereas as-1does not compete significantly even at 250 fold molar excess. Using a gel retardation assay for this factor it has been observed that the DNA protein complex can be competed with the wild-type but not the as-1c binding site. Thus, binding of ASF-1, if anything, was enhanced by mutation of the putative CAAT-box motifs and is abolished by mutation of a previously unrecognized repeat sequence, TGACG. Finally, it was found that the binding activity is sensitive to proteinase K and heat treatment (65° C.) indicating that ASF-1 is likely to be a protein factor.

The ASF-1 Binding Site Mutants Affect CaMV 35S Promoter Activity in Tobacco Protoplasts In order to determine the effect of diminished binding of ASF-1 in vivo the mutant binding sites as-1b and as-1c were placed in the context of the 35S promoter (-343 to +8) which was fused to the coding region of the bacterial chloramphenicol acetyltransferase (CAT) gene. The resulting 35S promoter sequences were identical to the wild-type sequence except for the four mutated base pairs. DNA was introduced into isolated tobacco leaf protoplasts by the PEG/MgCl$_2$ technique (9). The as-1b mutant consistently gives higher activity than the wild-type CaMV 35S promoter. On the other hand, activity of the as-1c mutant is drastically reduced. Since the enzyme activity assayed increases with increasing amounts of input plasmid DNA, these results are within the linear range of this assay system. Quantitation of the effects of the two mutations by extract titration showed that the as-1b containing promoter is about twice as active as the wild-type CaMV 35S promoter while the as-1c construct retains only 10% of the transcription activity. In this transient in vivo assay, therefore, activity correlates well with the relative binding affinity of ASF-1 for the mutated CaMV 35S promoters.

ASF-1 Binding Site Mutations Alter Characteristics of the CaMV 35S Promoter in Transgenic Plants The effect of inhibiting binding of ASF-1 on light responsiveness and organ specific expression in transgenic plants was determined. The CaMV 35S wild-type and mutant CaMV 35S promoter constructs used for the protoplast experiment were ligated into a vector that also contained a larger 35S upstream fragment (−941 to +8) driving the Beta-glucuronidase (GUS) coding sequence. The Poly A addition site (from the rbcS 3C gene) attached to the GUS coding sequence shares homology with the poly A addition site (from the rbcS E9 gene) fused to the CAT coding sequence. For this reason the CAT and the GUS mRNAs can be detected simultaneously using the same S1 probe (10). Seven independent transgenic plants which showed detectable expression in both the reference and the test genes were selected. Total RNA from light grown or dark adapted mature tobacco leaves from individual transgenic plants was then isolated and pooled for analysis. The wild-type CaMV 35S promoter (−343 to =8) shows a slight but reproducible increase in expression in light grown leaves as compared to dark adapted leaves. The mutations in as-1b eliminated the differences in mRNA levels between light grown and dark adapted leaves while the as-1c mutations decreased expression from dark adapted leaves to about one-fifth of that in the light as quantitated by RNA titration using the S1 nuclease protection assay. The expression of as-1b and as-1c in the light does not differ significantly from that of the wild-type promoter.

It has been reported previously that the −90 promoter fragment can confer low level expression in roots of transgenic plants. The organ specificity of the CaMV 35S promoter constructs were examined in mature transgenic plants in order to determine whether inhibition of ASF-1 binding was sufficient to reduce expression in stem or root. The wild-type CaMV 35S promoter gives similar levels of CAT activity in all three organs. The as-1b mutant shows a slight decrease in roots and stems relative to the expression in leaves. The as-1c CaMV 35S promoter mutant, however, exhibits much lower expression (between five and ten fold) in roots and stems and near wild-type expression in leaves. Expression in root was consistently far lower than expression in leaves, while stem expression showed greater variability. Similar results were obtained from five independent transgenic plants containing each construct and the data was corroborated by S1 protection analysis of root RNA from the transgenic plants. All the transformants showed high levels of GUS activity in the same root, stem and leaf extracts and the relative GUS activity of these extracts from a single transgenic plant did not differ by more than two fold. Thus, the as-1c mutations alter the organ specificity of the 35S enhancer by significantly attenuating expression in root tissues.

Introduction of ASF-1 Binding Site into a Green Tissue-Specific Promoter Causes High Level Expression in Root The involvement of the ASF-1 factor in maximal expression of the 35S promoter in root has been suggested by the correlation of mutations that block binding in vitro with decreased expression in vivo. In order to further support this correlation the wild-type and as-1c mutant binding sites were introduced into a promoter that normally does not express at detectable levels in root. The ribulose 1,5-bisphosphate carboxylase-3A (rbcS-3A) promoter is specific for green tissue and is highly expressed in light grown leaves and stems (11, 12). Previous work has identified several upstream elements essential for transcriptional activity of the rbcS-3A promoter (12). Since the spacing requirements and distance dependence of ASF-1 and the rbcS-3A elements are unknown, the ASF-1 binding site was added to the rbcS-3A promoter in two different ways. Briefly, in one case a 21 bp element (FIG. 4) containing either the wild type ASF-1 binding site or the as-Ic mutant was inserted into the -55 position of the rbcS-3A gene (constructs I and II, FIG. 3). In these constructs, the ASF-1 binding site is located at a similar distance to the TATA box element as in the 35S promoter but the sequence 5' to -55 in rbcS-3A are moved 25 bp upstream from the TATA element. In the second case, the ASF-1 binding site was inserted by base specific conversion between −89 and −109 of the rbcS-3A gene (constructs III and IV, FIG. 3). To accomplish this 10 out of 21 bases in this region were mutated to generate either a wild-type or as-1c mutant binding site for ASF-1. This construction preserved the known important elements of the rbcS-3A promoter, boxes II and III (10, 12), as well as their distance from the TATA region. However, ASF-1 is further away from the TATA box and bases of unknown importance were mutated. The insertion of the wild type ASF-1 binding site in either position of the rbcS-3A promoter results in substantial expression in the roots while insertion of the as-1c binding site does not result in increased expression. In leaves of light grown plants, high level expression is observed with both constructs. Similar results were obtained with constructs III and IV (8) indicating that the position of insertion of this binding site is not critical to increasing expression in roots.

These results demonstrate that the expression in roots is due to the binding of ASF-1 to the rbcS-3A promoter. Thus, introduction of a single ASF-1 binding site into a green tissue specific promoter can significantly alter the organ specific expression pattern in transgenic plants.

The above working examples are provided to better elucidate the practice of the present invention and should not be interpreted as limiting the scope of the present invention in any way. Those skilled in the art will recognize that modifications and alternate embodiments may be made while not departing from the spirit and scope of the present invention.

REFERENCES

1. Guilley, H., Dudley, R. K., Jonard, G., Balaze, E and Richards, K. E., *Cell* 30, 763 Balazs (1982).
2. Odell, J. T., Nagy F., and Chua, N. H., *Nature* 313, 810 (1985).
3. Ow, D. W., Jacobs, J. D. and Howell, S. H., *Proc. Natl. Acad. Sci. USA* 84, 4870 (1987); Odell, J. T., Knowlton, S., Lin W. and Mauvais, J. C., *Plant Mol. Biol.* 10, 263 (1988).

4. Fromm, M., Taylor, L. P. and Walbot, V., *Proc. Natl. Acad. Sci. USA* 82, 5824 (1985).

5. Odell, J. T., Nagy, F. and Chua, N. H., *Plant Gene Systems and Their Biology*, J. L. Key, L. McIntosh, Eds. (Alan R. Liss, Inc., New York, 1987) p. 321.

6. Fang, R. X., Nagy, F., Sivasubramaniam, S. and Chua, N. H., *The Plant Cell* in press (1989).

7. Poulsen, C. and Chua, N. H., *Mol. Gen. Genet.* 20 214, 16 (1988).

8 Lam, E., unpublished data.

10. Fluhr, R., Moses, P., Morelii, G., Coruzzi, G. and Chua, N. H., *EMBO* 5, 2063 (1986).

11. Fluhr, R., Kuhlemeier, C., Nagy, F. and Chua, N. H., *Science* 232, 1106 (1986).

12. Kuhlemeier, C. et al., *Proc. Natl. Acad. Sci. USA* 85, 4662 (1988).

We claim:

1. An isolated promoter element for enhancement of plant gene expression in roots consisting of the nucleotide sequence:

5'CTGACGTAAGGGATGACGCAC-3'.

2. A method for enhancing root expression of a plant gene containing a ribulose bisphosphate carboxylase small subunit promoter by inserting an isolated promoter element consisting of the nucleotide sequence 5'-CTGACGTAAGGGATGACGCAC-3' into a ribulose 1,5-bisphosphate carboxylase promoter.

3. A method of claim 2 in which the ribulose 1,5-bisphosphate carboxylase promoter is the ribulose 1,5-bisphosphate carboxylase-3A promoter.

4. A method of claim 3 in which the promoter element is inserted at position -55 of the ribulose 1,5-bisphosphate carboxylase —3A promoter gene.

5. A method of claim 3 in which the promoter element is inserted into positions —89 to —109 of the ribulose 1,5-bisphosphate carboxylase—3A promoter gene by site directed mutagenesis of the corresponding wild-type region.

* * * * *